(12) United States Patent
Beer et al.

(10) Patent No.: US 9,244,078 B2
(45) Date of Patent: *Jan. 26, 2016

(54) OXIDIZABLE SPECIES AS AN INTERNAL REFERENCE IN CONTROL SOLUTIONS FOR BIOSENSORS

(71) Applicant: Bayer HealthCare LLC, Whippany, NJ (US)

(72) Inventors: Greg P. Beer, Cassopolis, MI (US); Huan-Ping Wu, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,681

(22) Filed: Jan. 29, 2014

(65) Prior Publication Data

US 2014/0147872 A1    May 29, 2014

Related U.S. Application Data

(60) Continuation of application No. 13/180,214, filed on Jul. 11, 2011, now Pat. No. 8,702,926, which is a division of application No. 11/887,879, filed as application No. PCT/US2006/012940 on Apr. 7, 2006, now Pat. No. 8,002,965.

(60) Provisional application No. 60/669,729, filed on Apr. 8, 2005.

(51) Int. Cl.
G01N 33/66 (2006.01)
G01N 33/96 (2006.01)
G01N 27/327 (2006.01)

(52) U.S. Cl.
CPC ............ *G01N 33/66* (2013.01); *G01N 27/3274* (2013.01); *G01N 33/96* (2013.01); *Y10T 436/104998* (2015.01)

(58) Field of Classification Search
CPC .... G01N 33/96; G01N 33/66; G01N 27/3274
USPC .............. 204/403.01–403.15; 435/287.1, 14; 600/345–348; 422/82.01, 68.1
See application file for complete search history.

(56) References Cited

U.S. PATENT DOCUMENTS 3,920,580 A    11/1975 Mast .............................. 252/408
4,572,899 A     2/1986 Walker et al. ................... 436/18
(Continued)

FOREIGN PATENT DOCUMENTS

EP    0 741 186 B1    11/1996    ............... C12M 1/40
EP    0 762 112         3/1997    ............. G01N 21/47
(Continued)

OTHER PUBLICATIONS

Hall et al. (Analytical Biochemistry, vol. 26, 1968, pp. 12-17).*
(Continued)

*Primary Examiner* — Jennifer Dieterle
(74) *Attorney, Agent, or Firm* — Nixon Peabody LLP

(57) ABSTRACT

Testing of the performance of an electrochemical meter used to measure the presence of an analyte in a biological sample, particularly glucose in whole blood, includes introducing a control solution containing a predetermined amount of the analyte and a predetermined amount of an internal reference compound. The internal reference compound is selected such that it is oxidized at a potential greater than that used to oxidize the analyte, thereby making it possible to distinguish the control solution from a biological sample.

21 Claims, 11 Drawing Sheets

(56) References Cited

U.S. PATENT DOCUMENTS

| | | | |
|---|---|---|---|
| 4,729,959 A | 3/1988 | Ryan | 436/14 |
| 4,890,926 A | 1/1990 | Dosmann et al. | 356/369 |
| 5,028,542 A | 7/1991 | Kennamer et al. | 436/14 |
| 5,096,671 A | 3/1992 | Kane et al. | 422/82.07 |
| 5,120,420 A | 6/1992 | Nankai et al. | 204/403 |
| 5,155,628 A | 10/1992 | Dosmann | 359/640 |
| 5,320,732 A | 6/1994 | Fukuda et al. | 204/403.4 |
| 5,321,492 A | 6/1994 | Detwiler et al. | 356/73 |
| 5,361,314 A | 11/1994 | Kopelman et al. | 385/12 |
| 5,429,735 A | 7/1995 | Johnson et al. | 204/403 |
| 5,449,898 A | 9/1995 | Dosmann | 250/208.1 |
| 5,477,326 A | 12/1995 | Dosmann | 356/406 |
| 5,518,689 A | 5/1996 | Dosmann et al. | 422/82.05 |
| 5,520,786 A | 5/1996 | Bloczynski et al. | 204/403 |
| 5,605,837 A | 2/1997 | Karimi et al. | 436/14 |
| 5,611,999 A | 3/1997 | Dosmann et al. | 422/82.05 |
| 5,620,579 A | 4/1997 | Genshaw et al. | 204/402 |
| 5,627,922 A | 5/1997 | Kopelman et al. | 385/12 |
| 5,653,863 A | 8/1997 | Genshaw et al. | 205/777.5 |
| 5,660,791 A | 8/1997 | Brenneman et al. | 422/58 |
| 5,701,181 A | 12/1997 | Boiarski et al. | 356/446 |
| 5,723,284 A | 3/1998 | Ye | 435/4 |
| 5,798,031 A | 8/1998 | Charlton et al. | 204/403 |
| 6,157,442 A | 12/2000 | Raskas | 356/39 |
| 6,157,472 A | 12/2000 | Eum et al. | 359/18 |
| 6,181,417 B1 | 1/2001 | Dosmann | 356/326 |
| 6,272,262 B1 | 8/2001 | Kopelman et al. | 385/12 |
| 6,531,040 B2 | 3/2003 | Musho et al. | 204/401 |
| 6,535,753 B1 | 3/2003 | Raskas | 600/310 |
| 6,636,652 B1 | 10/2003 | Kopelman et al. | 385/12 |
| 7,132,041 B2 | 11/2006 | Deng et al. | 205/777.5 |
| 7,504,020 B2 * | 3/2009 | Tokunaga et al. | 205/792 |
| 8,002,965 B2 | 8/2011 | Beer et al. | 205/777.5 |
| 2001/0000129 A1 | 4/2001 | Raskas | 356/39 |
| 2001/0042683 A1 | 11/2001 | Musho et al. | 204/403 |
| 2002/0119507 A1 * | 8/2002 | Kishimoto et al. | 435/26 |
| 2002/0139692 A1 | 10/2002 | Tokunaga et al. | 205/777.5 |
| 2003/0149348 A1 | 8/2003 | Raskas | 600/310 |
| 2004/0060818 A1 * | 4/2004 | Feldman et al. | 204/403.01 |
| 2004/0061841 A1 | 4/2004 | Black et al. | 355/30 |
| 2004/0180444 A1 | 9/2004 | Rannikko et al. | 436/14 |
| 2004/0200720 A1 | 10/2004 | Musho et al. | 204/403.01 |
| 2004/0209371 A1 * | 10/2004 | Conlon et al. | 436/10 |
| 2005/0048599 A1 * | 3/2005 | Goldberg et al. | 435/34 |
| 2005/0247562 A1 | 11/2005 | Tokunaga et al. | 204/450 |
| 2008/0145878 A1 | 6/2008 | Marfurt | 435/14 |

FOREIGN PATENT DOCUMENTS

| | | | |
|---|---|---|---|
| EP | 1 156 324 A1 | 11/2002 | G01N 27/327 |
| EP | 0 800 086 B1 | 1/2003 | G01N 33/96 |
| EP | 1 557 662 | 7/2005 | G01N 27/26 |
| JP | 2001-208718 | 8/2001 | G01N 27/327 |
| JP | 2003-528313 | 9/2003 | G01N 27/416 |
| WO | WO 93/21928 A1 | 11/1993 | G01N 31/00 |
| WO | WO 95/13535 A1 | 5/1995 | G01N 31/22 |
| WO | WO 95/13536 A1 | 5/1995 | G01N 31/22 |
| WO | WO 01/71329 | 9/2001 | G01N 27/26 |
| WO | WO 2004/040286 * | 5/2004 | |
| WO | WO 2004/040286 A1 | 5/2004 | G01N 27/26 |
| WO | WO 2005/003622 A1 | 1/2005 | F17C 11/00 |
| WO | WO 2005/040407 A1 | 5/2005 | C12Q 1/00 |
| WO | WO 2005/045234 A1 | 5/2005 | |
| WO | WO 2005/078118 A1 | 8/2005 | C12Q 1/00 |
| WO | WO 2005/078437 | 8/2005 | G01N 33/487 |

OTHER PUBLICATIONS

International Search Report corresponding to International Patent Application Serial No. PCT/US2006/012940, European Patent Office, dated Aug. 29, 2006, 4 pages.

Hall, J.W. et al., "Automated Determination of Glucose using ENZ Glucose Oxidase and Potassium Ferro Cyanide ENZ Peroxidase," Analytical Biochemistry, vol. 26, No. 1, 1968, pp. 12-17.

Written Opinion corresponding to International Patent Application U.S. Appl. No. PCT/US2006/012940, European Patent Office, dated Aug. 29, 2006, 6 pages.

* cited by examiner

OXIDIZABLE SPECIES AS AN INTERNAL REFERENCE IN CONTROL SOLUTIONS FOR BIOSENSORS

CROSS-REFERENCE TO RELATED APPLICATIONS

This application is a continuation of U.S. application Ser. No. 13/180,214, issued as U.S. Pat. No. 8,702,926, filed Jul. 11, 2011, which is a divisional of U.S. patent application Ser. No. 11/887,879 filed Oct. 4, 2007, which is a U.S. national stage of International Application No. PCT/US2006/012940 filed Apr. 7, 2006, which claims priority to Application No. 60/669,729 filed on Apr. 8, 2005, all of which are incorporated in their entirety.

FIELD OF THE INVENTION

This invention is directed generally to the field of medical devices.

BACKGROUND OF THE INVENTION

More specifically, this invention relates to the biosensors that are used to measure the amount of analytes in bodily fluids. Optical methods are often used for making such measurements, but the present invention relates to improvements in electrochemical biosensors. While the method to be described herein can be applied to measurement of other analytes, including cholesterol, urea, creatinine, and creatine, measuring glucose in whole blood is of particular interest. Although the description here will emphasize the inventions application to measuring glucose, it should be understood that the invention has broader applications.

The invention relates to an electrochemical instrument in which a potential is applied to electrodes in contact with a biological sample and reagents. The resulting current is measured while the analyte is reacting with the reagents, and then correlated with the amount of an analyte in the sample. Such instruments are referred to as amperometric, in contrast with coulometric instruments that measure the total charge in coulombs produced from reaction of the sample by integrating the current over the entire measurement time. The amperometric instruments have an advantage in that they are less volume and time dependent. They do not wait for the entire volume of the analyte to be reacted, but only take measurements of the analyte by sampling the reaction rate at a predetermined time.

Many designs for such biosensors have been described in the art, for example, published U.S. Patent Application 2001/0042683. The electrodes are generally described as the working electrode and as the counter electrode. The electrodes are in contact with a solid layer containing reagents that oxidize the analyte in the sample, such as glucose oxidase, and mediators that reoxidize the reduced enzyme. The reduced mediator itself is oxidized at the working electrode, which produces a measurable current. This current is used to calculate the amount of glucose in the sample being tested, since it is an indirect measure of the oxidation of glucose in the sample. The reactions may be described by the following steps:

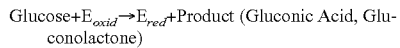

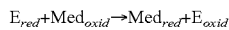

Where $E_{oxid}$ and $E_{red}$ are oxidized and reduced forms of the redox center of the enzyme and $Med_{oxid}$ and $Med_{red}$ are the oxidized and reduced forms of the mediator.

For measuring glucose, the enzyme may be glucose oxidase and the mediator ferricyanide. Measuring other analytes will employ suitable enzymes and mediators. Typical combinations of enzyme, mediator and analyte are listed in Table 1.

TABLE 1

Selected Substrates, Enzyme and Mediator Systems

| Analyte | Enzyme | Mediator |
|---|---|---|
| Glucose | Glucose Oxidase | Ferricyanide |
| Glucose | Glucose Dehydrogenase | Ferricyanide |
| Cholesterol | Cholesterol Oxidase | Ferricyanide |
| Lactate | Lactate Oxidase | Ferricyanide |
| Uric Acid | Uricase | Ferricyanide |
| Alcohol | Alcohol Oxidase | Phenylenediamine |

In order to assure accurate measurements, control solutions containing known amounts of glucose are used to verify that the instrument is operating properly. The composition of control solutions has been the subject of a number of patents and publications. Representative are U.S. Pat. Nos. 3,920,580; 4,572,899; 4,729,959; 5,028,542 and 5,605,837; WO 93/21928; WO 95/1.3535; and WO 95/13536. While control solutions containing blood serum have been used, more recent patents have been concerned with replacing serum-based control solutions with solutions free of serum, since serum-free solutions are more consistent and stable than those containing serum. The control solution should contain a known concentration of glucose in a serum-like matrix to determine the accuracy of both the enzymatic biosensor and the potentiostat meter. It will be evident that the composition must be stable over lengthy periods of storage before use.

Control solutions should serve the purpose of checking the glucose monitoring system's functioning, but at the same time they should be identified and separated from the readings of real blood samples. This is because the control solutions contain known amounts of glucose and provide readings that have no therapeutic purpose. If the control solutions cannot be identified and their responses separated from those of the blood samples by the test meter, glucose readings of the control solutions will be included in the history of the glucose measurements, which could lead to wrong interpretation of a patient's diabetic condition. Or, if a control solution is substituted for a blood sample, it may be mistakenly considered by a physician as indicating a need to change treatment. Furthermore, since the temperature response of the control solutions is different from that of the blood samples, temperature compensation for measurements made at temperatures other than 25° C. will be less accurate if a test meter cannot distinguish between blood samples and control solutions. Therefore, it is highly desirable that the glucose monitoring system automatically detect and identify the control solutions in order to separate the glucose readings of control solutions from those of the blood samples, and to provide separate temperature compensation to both the blood samples and the control solutions.

There have been several patents describing methods of identifying the control solutions through various mechanisms. In U.S. Pat. No. 5,723,284, electrochemical measurement of glucose in blood is discussed. The '284 patent proposed to modify the control solutions, changing the ratio of current readings taken from two oxidation periods separated by a rest period. The meter would recognize that a control solution was being measured and take appropriate action to prevent the results from being included in the blood sample results. The '284 patent also teaches that the control solution should be buffered in a pH range of 4.8 to 7.5 to be effective.

Another method for determining whether a control solution or a blood sample is being measured for its glucose content is disclosed in U.S. Published Application 2002/0139692A1. An index is determined, that relates the decline of electrical current to the nature of the sample being tested.

U.S. Pat. Nos. 5,620,579 and 5,653,863, proposed to begin the test of a sample by providing, an initial positive potential pulse for a short period in order to reoxidize any prematurely reduced mediator. Such an initial pulse was referred to as a "burnoff period".

When a potential is applied across the working, and counter electrodes and a liquid sample is introduced to the sensor, the dry reagents are rehydrated by the liquid sample and current begins to flow, typically increasing to a peak and then declining over the "burn period," usually about ten seconds in length. During this period the previously reduced mediator is reoxidized to reduce the bias towards incorrect high results. If a full amount of sample is not present, additional error may be introduced since all of the reagents may not become available for reaction or the working and counter electrodes might not be in complete contact with sample, thus reducing the current during the "burn" period.

After the burn period has been completed, a rest period is provided at a lower potential or at no potential (open circuit). During this rest period the glucose oxidation reaction continues to take place and the mediator is reduced. Then, a constant potential is applied again between the working and counter electrodes and the current is measured for a short period, typically about two to ten seconds. The current is initially high, but it declines rapidly as diffusion of the mediator begins to control. At a predetermined time, the measured current is used to determine the glucose content of the sample.

Adding an internal reference compound is a common practice in analytical chemistry to provide a quantitative reference signal. This working principle has been used in a recent published patent application No. WO 2005/078118, where an internal reference is added to the reagent system to achieve some formulation purpose.

In WO2004/040286A1, it is proposed that the control solution include a reducing substance chosen from uric acid, bilirubin, ascorbic acid, methylene blue, Bis(2-hydroxyethyl)iminotris(hydroxymethyl)methane, N,N-bis(2-hydroxyethyl)-2-aminoethane sulfonic acid, and acetaminophen, thus changing the ratio of current readings taken from two oxidation periods separated by a rest period and enabling the control solution to be identified.

The present inventors have sought an improved method of distinguishing control solutions from biological samples. Their methods are described in detail below.

SUMMARY OF THE INVENTION

This invention provides a method for distinguishing a control solution from a biological sample during the operation of an electrochemical meter through a quantitative index. In one embodiment, the invention is a control solution which includes known amounts of glucose, a buffer system with a suitable pH value, and an internal reference compound. The internal reference compound is added to the control solution to identify the control solution by the glucose monitoring system. The invention provides a method of detecting the presence of the internal reference compound, calculating the quantitative index, and identifying that a control solution is being tested.

In one embodiment, the analyte in the biological sample is glucose in whole blood and the mediator is potassium ferricyanide. The internal reference compound is oxidizable at a potential higher than the potential required to oxidize the mediator, which is used to measure the oxidation of analyte. The internal reference has a predetermined concentration in the control solution along with a predetermined concentration of glucose. The glucose-related mediator and the internal reference are selectively oxidized at the electrode by different potentials (low and high). When glucose is the analyte, the internal reference compound should be oxidizable at a potential of at least 100 mv higher than the potential used to re-oxidize the reduced mediator.

Internal reference compounds useful for measuring glucose in control solutions include any species oxidizable at the electrode at an appropriate potential such as organo-metallic compounds, coordination compounds, and organic amine compounds. The amount of the internal reference compound used is related to the amount of glucose in the control solution. Preferably, the amount of the internal reference compound is chosen so that the control solution can be recognized when the glucose in the control solution is the maximum required to test the electrochemical glucose meter. Alternatively, the amount of the internal reference compound can be varied in proportion to the amount of glucose.

Comparing measurements made at low and high potentials provides a method to detect the internal reference compound and thus the control solution. When the measurement protocol employs two periods separated by a rest period, the high and low voltages can be applied in either period or both. A potential is applied, to a sensor that has received the control solution. The current produced at a potential capable of oxidizing the internal reference compound is compared with the current produced when a potential capable of oxidizing only the analyte glucose), but not the internal reference compound. The ratio between the two measured currents, designated the Differential Index (DI), provides a means for distinguishing the control solution from a liquid sample lacking the internal reference compound.

$$DI = i_{high\ volt}/i_{low\ volt}$$

where $i_{high\ volt}$ and $i_{low\ volt}$ are the currents measured at high and low voltages.

At the higher voltage, both the internal reference compound and the reduced mediator are oxidized, while at the lower voltage only the mediator is oxidized, A DI value of about 1 indicates that the sample lacks the internal reference compound and is presumed to be a biological sample, while a DI value significantly greater than 1, preferably at least about 1.5, indicates that the sample is a control solution.

In another embodiment, the invention is an internal reference compound suitable for indicating the presence of a control solution being used to test the accuracy of an electrochemical biosensor/potentiostat system. Where the analyte is glucose in whole blood the internal reference compound maybe an oxidizable organo-metallic compound, a coordination compound, or an organic amine.

One result of the present invention is the improvement of the consistency of the current measured and the accuracy of the resulting analysis. If high and low potentials are applied during the same oxidation period, such as the burn and read periods used in oxidation of glucose, it is less likely that external factors, such as sample movement or environmental temperature will affect the Differential Index. Multiple readings of the current developed at high and/or low voltages can improve the accuracy of the results. Also, when the presence of a control solution has been determined, a temperature correction algorithm particular to the control solution can be applied. By using different temperature algorithms for the control solution and the biological sample, (e.g., whole blood), clinical results can be improved and tighter control range values can be assigned.

DETAILED DESCRIPTION OF THE DRAWINGS

Description of the Preferred Embodiments

The invention will be described below as applied to measuring the glucose content of whole blood, a method of commercial importance. However, the method of the invention has other applications where other analytes such as cholesterol, urea, creatinine, and creatine are found in biological fluids such as urine, saliva, and interstitial fluid, and where control solutions are used to check the accuracy of electrochemical meters.

Electrochemical Biosensors

The present invention is not limited to a particular biosensor design among the many that have been disclosed in the art. An example of a biosensor which may be used is described in U.S. Pat. No. 6,531,040, which is illustrated in FIGS. 1 and 2.

Figure 1:
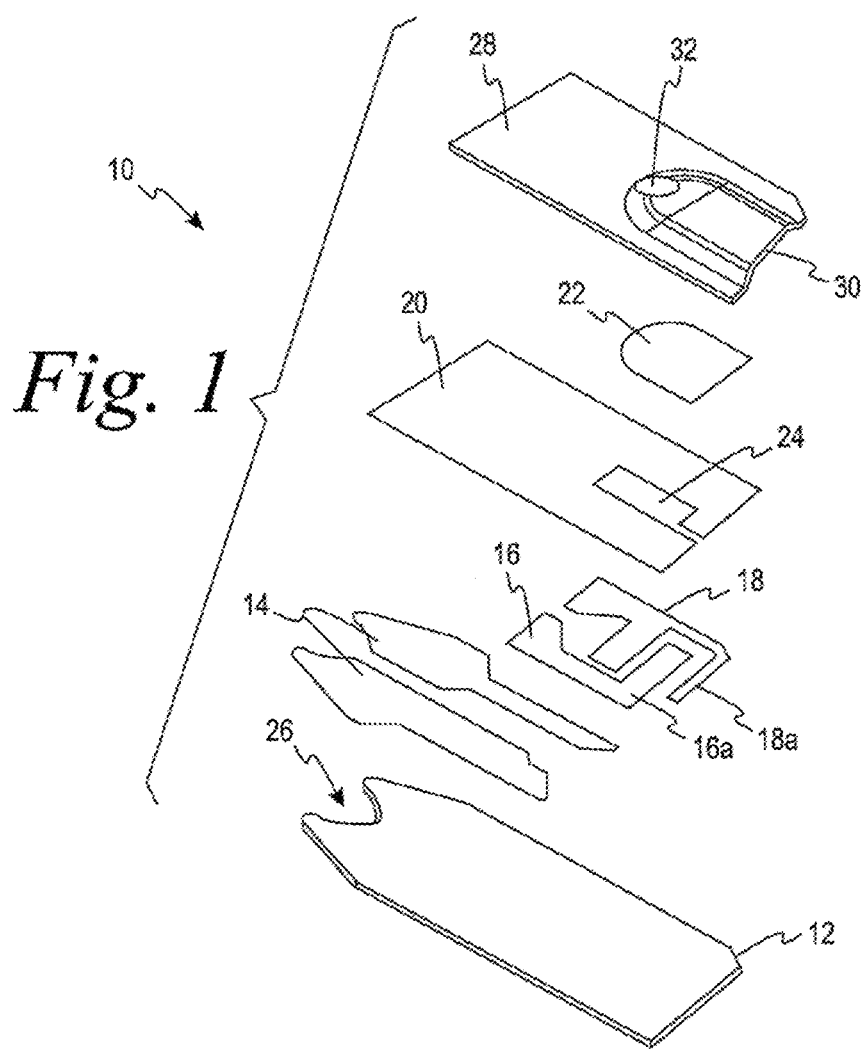
FIG. 1 is an exploded view of a biosensor according to one embodiment.
Figure 2:
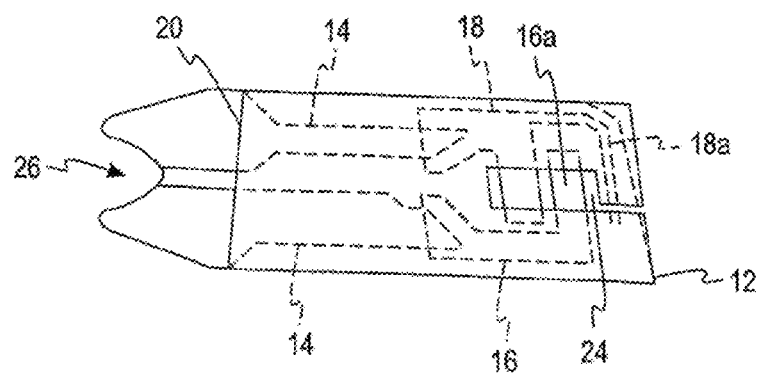
FIG. 2 is an assembled view of the biosensor of FIG. 1.

The biosensor 10 is shown in an exploded view in FIG. 1. It comprises an insulating base 12 upon which is printed in sequence (typically by screen printing techniques), an electrical conductor pattern 14, an electrode pattern (portions 16 and 18), an insulating (dielectric) pattern 20, and a reaction layer 22, and completed by a cover layer 28. The capillary 30 formed between the cover layer 28 and the reagent layer 22, provides a flow path for the fluid test sample. The biosensor is shown in FIG. 2 in which all of the elements on the base are shown in the same plane.

The function of the reaction layer 22 is to effect a chemical reaction with glucose, or another analyte in the fluid test sample, and to produce an electrical current which is measured and correlated with the amount of the analyte present. The reaction layer 22 typically contains an enzyme or enzymes, and an electron acceptor. The enzyme reacts with the analyte to produce electrons, which are conveyed to the surface of the working electrode by an electron acceptor. The electron acceptor, also referred to as a mediator, which is reduced in response to the reaction between the analyte and the enzyme. The enzyme in the reaction layer may be combined with a hydrophilic polymer, such as polyethylene oxide. One enzyme that may be used to react with glucose is glucose oxidase and the mediator may be a ferricyanide salt, used with a buffer maintaining a pH of about 5-7. Another enzyme that may be used is glucose dehydrogenase, along with a co-factor such as pyrroloquinoline quinone (PQQ), used with a buffer maintaining a pH of about 6-8.

The two portions 16, 18 of the electrode pattern provide the respective working and counter electrodes necessary to electrochemically determine the analyte's concentration. A feature of the design shown is that the working and counter electrodes are configured such that the major portion of the counter electrode is located downstream (in terms of the direction of fluid flow along the flow path) from the exposed portion of the working electrode 16a.

Counter electrode sub element 18a, however, is positioned up stream from working electrode upper element 16a so that when an amount of the test fluid sample (e.g., a whole blood sample) inadequate to completely cover the working electrode enters the capillary space, an electrical connection forms between counter electrode sub-element 18a and exposed portion of the working electrode 16a due to the conductivity of the whole blood sample. The area of the counter electrode, however, that is available for contact by the whole blood sample is so small that only very weak current can pass between the electrodes and, thus, through the current detector. When the received signal is below a certain predetermined level, the sensor device informs the user that insufficient blood had entered the sensor's cavity and that another test should be conducted, or that more blood should be added. While the particular dimensions of the electrodes are not critical, the area of the counter electrode sub-element 18a is typically less than about 10% than that of the working electrode and more specifically, less than about 6%.

The working and counter electrodes are generally printed using electrode ink, which is generally about 14 µm (0.00055') thick and typically contains electrochemically active carbon. Components of the conductor ink may be a mixture of carbon and silver that is chosen to provide a low conductive resistance path between the electrodes and the meter with which they are in operative connection via contact with the conductive pattern at a fish tail end 26 of the sensor. The counter electrode may be comprised of silver/silver chloride although carbon is preferred. To enhance the reproducibility of the meter reading, the dielectric pattern insulates the electrodes from the fluid test sample except in a defined area near the center of the electrode pattern 24. Referring to FIG. 2, a defined area is important in this type of electrochemical determination because the measured current depends not only on the analyte concentration and the area of the reaction layer 22, but also on the area of the working electrode 16a that is exposed to the analyte-containing test sample.

A typical dielectric layer 20 comprises a UV-cured acrylate modified monomer, oligomer or polymer, and is about 10 µm (0.0004') thick. The dielectric layer also may be moisture-curable or heat-curable. A lid or cover 28 is adapted to mate with the base to form a space to receive the fluid test sample in which the counter and working electrodes are situated. The lid 28 provides a concave space 30, and is typically formed by embossing a flat sheet of deformable material. The lid 28 is punctured to provide an air vent 32 and joined to the base 12 in a sealing operation. The lid and base can be sealed together by sonic welding in which the base 12 and lid 28 are first aligned and then pressed together between a vibratory heat sealing member or horn and a stationary jaw. Contact is made only with the flat, non-embossed regions of the lid. Ultrasonic energy from a crystal or other transducer is dissipated as heat in the polymeric joint allowing the bonding of the thermoplastic materials. The embossed lid and base may also be joined by using an adhesive material on the underside of the lid. The method of joining the lid and base is more fully described in U.S. Pat. No. 5,798,031.

Suitable materials for the insulating base 12 include polycarbonate, polyethylene terephthalate, dimensionally stable vinyl and acrylic polymers, and polymer blends such as polycarbonate/polyethylene terephthalate, and metal foil structures (e.g., a nylon/aluminum/polyvinyl chloride laminate). The lid typically is fabricated from a deformable polymeric sheet material such as polycarbonate, or on embossable grade of polyethylene terephthalate, glycol modified polyethylene terephthalate, or a metal foil composition (e.g., an aluminum foil structure).

Other electrochemical sensor designs may be used in the present invention. Examples of an electrochemical sensor that can be used to measure glucose concentrations are those used in Bayer HealthCare's Ascensia™ DEX® and ELITE® systems. More details on such electrochemical sensors may be found in U.S. Pat. No. 5,120,420 and U.S. Pat. No. 5,320,732. Other electrochemical sensors are available from Matsushita Electric Industrial Company. A further example of an electrochemical sensor that may be used in an amperometric monitoring, system is disclosed in U.S. Pat. No. 5,429,735.

The electrochemical sensors may be located in a blood glucose sensor dispensing instrument loaded with a plurality of sensors or testing elements. One example of a sensor pack loaded in a sensor dispensing instrument is disclosed in U.S. Pat. No. 5,660,791.

Measuring Glucose in Whole Blood

In a typical biosensor for measuring the glucose content of whole blood, the working and counter electrodes are coated with a single layer of reagent either by co-printing or co-depositing. The reagent layer will typically include some polymers and the reactive ingredients, that is, an enzyme which oxidizes the glucose in the blood sample and a mediator, i.e. a redox compound that re-oxidizes the enzyme after it has been reduced by oxidizing glucose. The reduced mediator carries electrons from the enzymatic reaction of glucose oxidation to the working electrode and is re-oxidized at the electrode surface. The applied voltage differential between the two electrodes results in the mediator passing electrons to the working electrode, creating a measurable current which is proportional to the amount of glucose in the sample. The biosensor also may comprise multiple reagent layers, or may comprise different single or multiple reagent layers at each electrode, working and counter electrodes.

Figure 3:
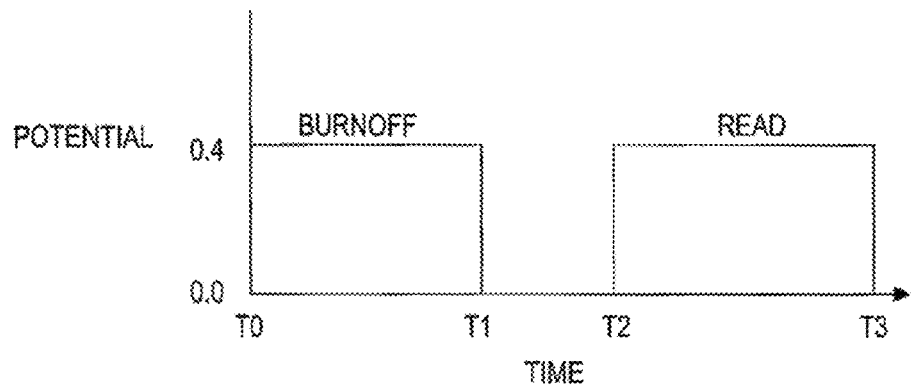
FIG. 3 is one plot of potential versus time for a burn period.
Figure 4:
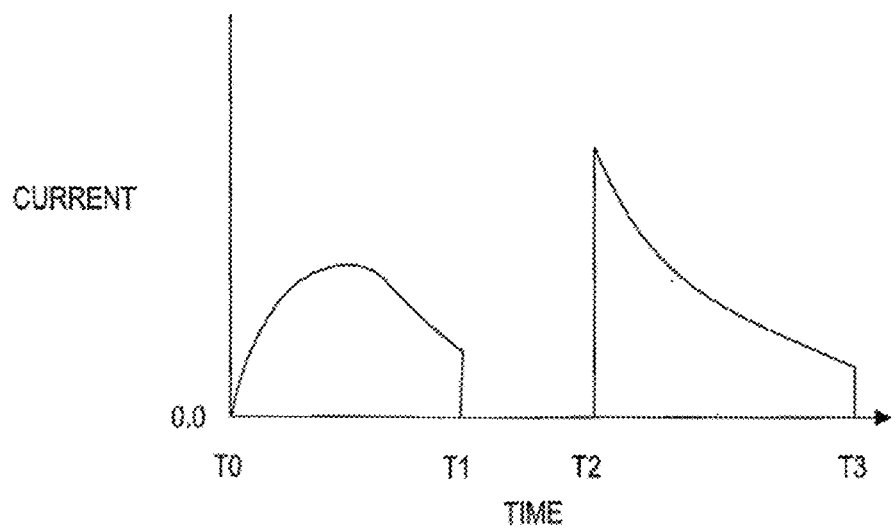
FIG. 4 is one plot of current versus time for the potential applied as FIG. 3.

As previously described, the amperometric sensors apply a fixed potential across the electrodes and the current produced is measured over a predetermined period of time, which may be quite short, say 5 to 10 seconds, in order to correct for the bias that may be present due to premature reduction of the mediator. In a preferred system a potential is applied for two periods of time, separated by a rest period. A representative plot of the potential versus time for the first or "burn period" is presented in FIG. 3. FIG. 4 shows a representative plot of current versus time that results. The current rises to a peak while the sample is rehydrating the reagent layer, enabling the oxidation and reduction reactions to occur and then declines as diffusion begins to control. After this brief period, the applied potential is removed or at least reduced during a resting period, while the oxidation of glucose and reduction of the mediator continue. Then, the potential is reapplied for a second period and the current measured over the "read" period, (e.g., ten seconds). Since reduced mediator is present as the result of the concomitant oxidation of the enzyme, the current produced initially is high, but then it declines rapidly and approaches a steady state diffusion-controlled condition. The current recorded at the end of the short "read" period is used to determine the glucose content of the blood sample, through a previously obtained correlation between the current at the end of the read period and the glucose contained in test samples having known concentrations.

Control Solutions

As previously discussed, various approaches have been taken to assure that a control solution provides accurate readings and can be distinguished from a biological sample. The present invention employs an oxidizable species (i.e., an internal reference) that is oxidizable only at voltages higher than those used for glucose (or other analyte) measurements. This means that at a low potential adequate to fully oxidize the glucose-related mediator, but not the internal reference compound, only the glucose will be measured. However, when the potential is high enough to oxidize the added internal reference compound, both the glucose and the internal reference compound will be oxidized. Although glucose is oxidized at the higher potential, the measurement made at a lower voltage is already diffusion-limited and does not depend on the total amount of glucose oxidized by the enzyme. It is feasible, therefore, to add such internal reference species to a control solution and to use it to identify the solution as a control and not as a biological sample.

The difference between the currents measured at high and low voltages can be compared to indicate the presence of the internal reference characteristic of the control solution. The Differential index (DI) following current components relating to the glucose and the internal reference compound:

$$DI = i_{high\ volt}/i_{low\ volt} = (i_{int\ ref} + i_{glucose})/i_{glucose} = 1 + i_{int\ ref}/i_{glucose}$$

where $i_{high\ volt}$ is the current measured at the higher voltage
$i_{low\ volt}$ is the current measured at the lower voltage It follows that if the internal reference is not present (such as in the blood samples), $i_{int\ ref}$ should be zero and the $i_{high\ volt}$ will be substantially the same as $i_{low\ volt}$. Thus, the DI value will approach 1. When the internal reference is present, the value of DI will be greater than 1, depending on the amount of the reference compound relative to the amount of glucose. If the amount of internal reference added to the control solution provides a current similar to that from oxidizing the glucose-related mediator, the DI value can be about 2. The internal reference may be included in an amount suitable for control solutions corresponding to a high glucose concentration. It is typical to use several control solutions corresponding to low, normal, and high glucose concentration to test a glucose meter. If, for example the amount of the internal reference is chosen so that the DI value is 1.75 or greater for the highest glucose concentration in the control solution, the current from the internal reference will be relatively large compared to the current for the glucose in the lowest glucose control solution. Then the same amount of the Internal reference used with a control solution having a low glucose concentration will provide an even higher value of DI. Such high DI values will provide higher confidence in the presence of a control solution, rather than a biological sample, such as whole blood. Clearly, a quantitative index such as the DI value has an advantage over the more qualitative methods of relying on the shape of the current versus time curve in the burn or read periods, as suggested in other patents. The addition of an internal reference oxidized at a higher voltage provides a result that is independent of the enzymatic reaction and the composition of the control solution.

In one embodiment, the amount of the internal reference compound added to the control solution is related to the amount of glucose present. That is, the amount of the internal reference in the control solution is proportional to the glucose concentration to maintain an approximately constant DI value. One method is to use enough of the internal reference to provide a DI of about 1.5 or higher when the maximum amount of glucose at about 300 mg/dL is used. Then, the amount of the internal reference is reduced so that control solutions containing lower concentrations of glucose maintain a DI value of 1.5 or higher.

Adding an internal reference to control solutions makes it possible to readily distinguish between control solutions and biological samples and provides improved accuracy of the analysis. Internal reference compounds can be any compound oxidizable electrochemically at a desirable potential. It is important to understand that not all compounds oxidizable chemically are oxidizable electrochemically at an appropriate potential or at any oxidizable potential. Chemically oxidizable species in a homogeneous solution) may not be oxidizable electrochemically at an appropriate potential because the electron transfer kinetic barrier at the electrode has to be overcome. Thus, a reducing agent by chemical nature may not be electrochemically oxidizable at the electrode. Depending on the redox potential of the mediator in the reagent sensor system, internal reference compounds with different redox potentials will be needed. For instance, if the mediator in the reagent system is ruthenium hexaamine (Ru(NH3)6+3), the coordination compound potassium ferrocyanide or the organo-metallic compounds ferrocene and its derivatives can be used as the internal reference in the control solution. On the other hand, if the mediator is ferricyanide in the reagent system, then other compounds such as the Bis-Tris or 4-amino benzonitrile can be used as the internal reference in the control solution. In each case, the internal reference compound will have a redox potential that is at least 1.00 mV higher than the redox potential of the mediator.

Examples of the internal reference compounds include, but are not limited to, organic amines such as 3-(N-morpholino) propane sulfonic acid [MOPS], N-(2-hydroxy ethyl) piperazine-N'-(2-ethane sulfonic acid) [HEPES], 2-[-Hydroxy-1,1-bis(hydroxymethyl)ethyl amino]ethane sulfonic acid [TES], 2-Morpholinoethane sulfonic acid [MES], Bis(2-hydroxyethyl)amino-tris(hydroxymethyl)methane [Bis-Tris], 4-Amino benzonitrile, 4-Amino benzoic acid, and 4-Iodoaniline. In the examples below, Bis Tris and several other compounds are shown to be a useful internal reference for use in control solutions containing glucose.

Although Bis-Tris can be used as an internal reference, it also can serve as a buffer. The pH of the control solution is an important factor in the reaction in which glucose is oxidized by an enzyme, such as glucose oxidase. For the measurement of glucose, a pH of about 5 to 7 is preferred when glucose oxidase is used, while a pH of about 6-8 is preferred when glucose dehydrogenase used. A buffer is usually provided to assure that the oxidation of glucose proceeds at the expected rate. An advantage of the present invention is that the reference compound and the buffer can be separate, with each serving a different function, thus enabling the optimization of each function (buffer and internal reference) separately. The buffers may be chosen from those compatible with the enzymatic reagent. Examples include, but are not limited to, citrate buffer and phosphate buffer.

The polymeric materials used to mimic the blood's fluidic properties may include polyethylene oxide, polyhydroxyethyl methacrylate, polyvinyl pyrolidone xanthan gum, in amounts of about 12 to 20 wt %. The glucose is typically present in control solutions in the amounts equivalent to about 30 to 400 mg/dL, a range that spans the expected glucose content of blood samples.

Other additives may include salts, buffers, dyes, anti-microbial agents, polymers, thickening agents, and surfactants.

Mode of Operating the Control Solution

It will be obvious that introducing an internal reference material oxidizable at a higher voltage than is used to oxidize the glucose-related mediator will make it necessary to apply the higher voltage at some point during the measurement protocol. Where two periods are used as described above, that is "burn" and "read" periods, various combinations of potential steps within and across the burn and read periods can be used to provide both a DI value identifying the control solution and a current from which the glucose content of the control solution could be determined. In the simplest method, a high voltage is applied during the burn period and a low voltage is applied during the read period. Thus the Differential Index is:

$$DI=i_{burn}/i_{read}$$

When the internal reference is present, the current measured during the burn period would include the current resulting from oxidization of the internal reference plus the current resulting from oxidizing the glucose-related mediator. The current measured during the read period would only be that resulting from oxidation of the glucose, since the voltage would be too low to oxidize the internal reference. Thus, the ratio of burn current to read current reflects the value of the internal reference current against the current of glucose measurement.

Alternatively, both high and low voltages could be applied during the burn period to detect the presence of the internal reference, while only a low voltage is used during the read period. This combination of potential steps would still maintain the working principle of taking the ratio of the current from a high voltage to that from a low voltage. A distinct change in the current would be seen when a change is made from a low voltage to a high voltage or vice versa. The "low" voltage need not be identical with that used in the read period to measure glucose. The comparative voltage could be merely lower than needed to oxidize the internal reference. Since the burn period corresponds to a time when the sample is hydrating the reagents, the current may change during the burn period, as suggested in the generic, diagram of FIG. 4. Consequently, there may be an advantage to making more than one excursion between high and low voltages to assure that the DI values are not affected by changes in the reagent availability during the burn period.

In another alternative method, a high voltage (i.e., one that oxidizes the internal reference) is used during a portion of the read period. Thus, the DI may be determined during the read period by measuring the high and low currents only during the read period. This method may provide an advantage in that any variation in reagent availability seen in the burn period are avoided. Again, using more than one excursion between low and high voltages may be advantageous.

In another embodiment of the invention, frequent cycling of potential between high and low voltages is used to affect the shape of the current versus time during the read period, which is shown generically in FIG. 4. The curve typically shows a rapid decay of the current caused by the depletion of the reduced mediator at and near the electrode surface. Thus, the total glucose content is determined by correlation with the diffusion-limited, current, rather than measuring the total glucose in the control solution. It is evident that the time chosen as a measure of the glucose is important if consistent and accurate measurements are to be obtained.

In general, control solutions of the invention will contain a compound that can be oxidized electrochemically at a potential greater than that needed to oxidize glucose. Since oxidation of the glucose related mediator (e.g., potassium ferricyanide) requires a potential of 200 mV relative to the potential at the counter electrode of ferricyanide, the oxidation potential for the internal reference compound should be at least 400 mV relative to the same counter electrode. For example, using Bis-Tris as the reference, the oxidation potential is about 600 mV if the counter electrode is supported by the reduction of ferricyanide. Other examples include 4-amino benzonitrile, 4-aminobenzoic acid, 4-iodoaniline, which can also be oxidized in a potential range of +400 to +600 mV relative to the potential at the counter electrode supported by the reduction of the ferricyanide.

One method of examining the effect of adding an internal reference to control solutions is using cyclic voltammetry. Instead of applying a fixed potential, a varying voltage is used, sweeping from negative to positive relative to the counter electrode. The following examples illustrate the concept and application of internal reference and its method for auto-detection of control solutions.

Example 1

Figure 5:
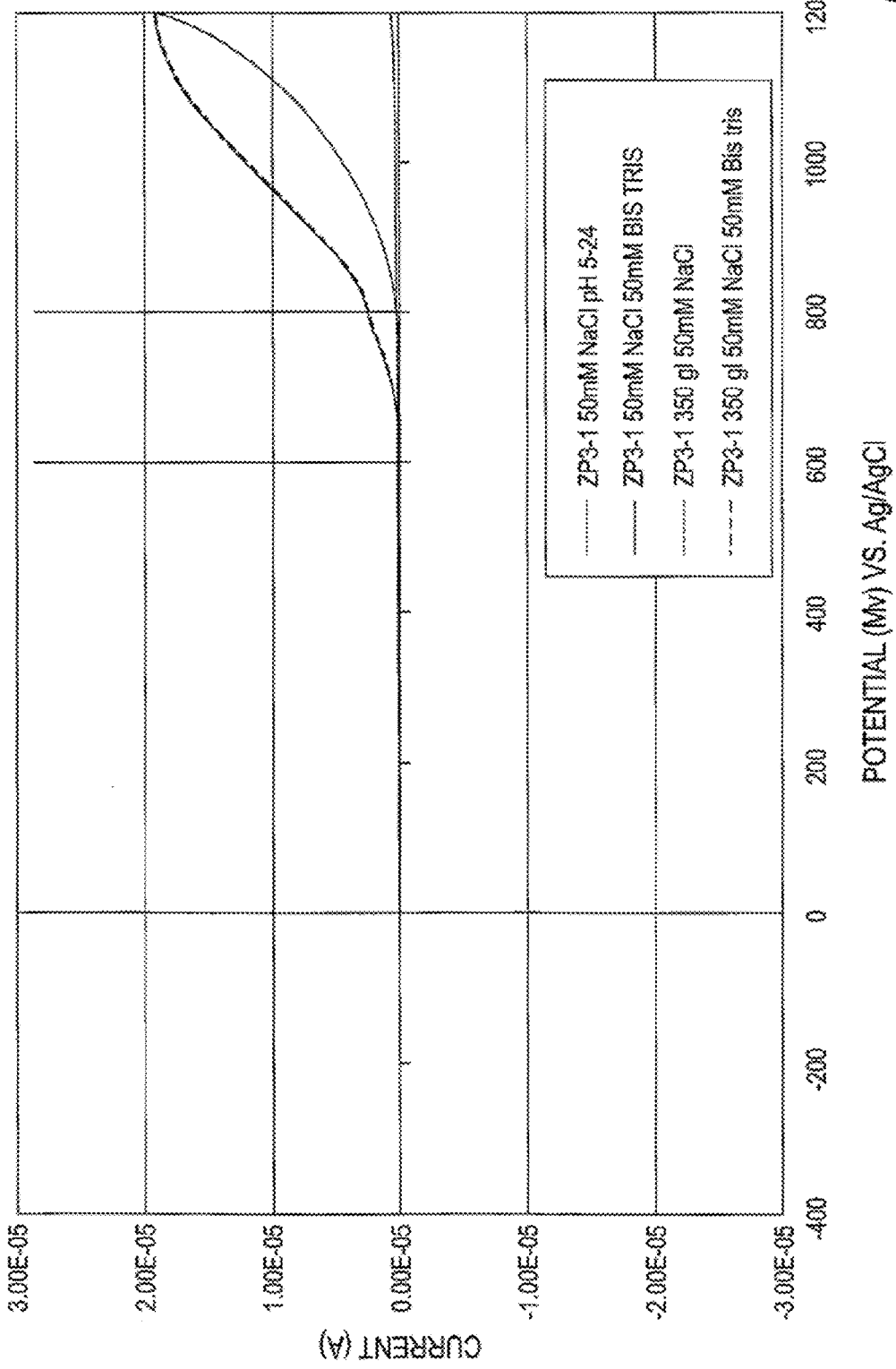
FIG. 5 is a cyclic voltammogram described in Example 1.

An aqueous solution containing 50 mM NaCl was compared with another solution containing 50 mM NaCl and 50 mM Bis-Tris as an internal reference. A second set of samples containing the same composition, but including 350 mg/dL glucose, was tested. No enzyme or mediator was included, so that oxidation of glucose did not occur. FIG. 5 shows the current versus potential as the potential difference was cycled between −400 my and +1200 mV at 25 mV/sec versus a silver/silver chloride reference electrode using the electrochemical work station of CH instrument Co. It can be seen that the current did not begin to flow between the electrodes until a potential difference of +600 mV was reached. For the samples containing no Bis-Tris, the oxidation current is substantially zero throughout the potential range. On the other hand, when Bis-Tris was present, there was a significant current at +800 mV, beginning at about +600 mV. It can be concluded that that the oxidation of Bis-Tris is the same with and without glucose present when no enzyme and mediator are present. When comparing the voltammetric currents at +800 mV between voltammograms with and without Bis-Tris in FIG. 5, the solutions containing 50 mM Bis-Tris were clearly distinguished.

Example 2

Figure 6:
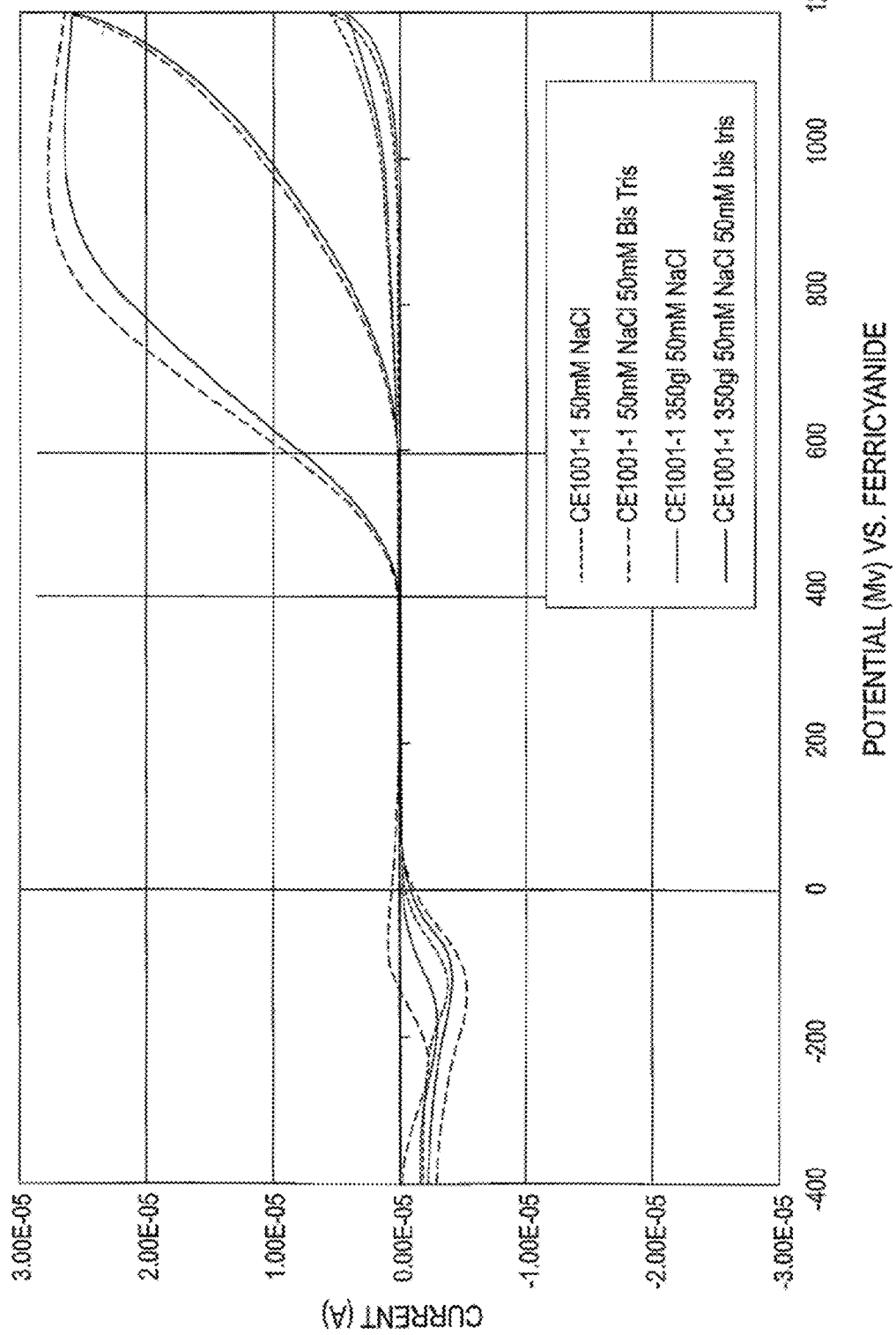
FIG. 6 is a cyclic voltammogram described in Example 2.

In this example, the tests of Example 1 were repeated, as shown in FIG. 6, except that the counter electrode was carbon with a layer of potassium ferricyanide, rather than the Ag/AgCl$_2$ counter electrode used in Example 1. The oxidation of Bis-Tris is not affected by the presence or absence of glucose, when enzymes and mediators are not included. However, the oxidation current starts to rise after +400 mV and reaches a significant magnitude at +600 mV. Thus, compared to the voltammetric features in FIG. 5, the background currents remain substantially zero without the internal reference. The only difference is the rise of the oxidation current at a lower potential. This difference is entirely due to the different counter electrode. It is significant that there is no oxidation current below +400 mV. Thus, Bis-Tris can be seen to be dearly distinguished from glucose oxidation, which begins just above zero potential, as will be seen in the next example.

Example 3

Figure 7:
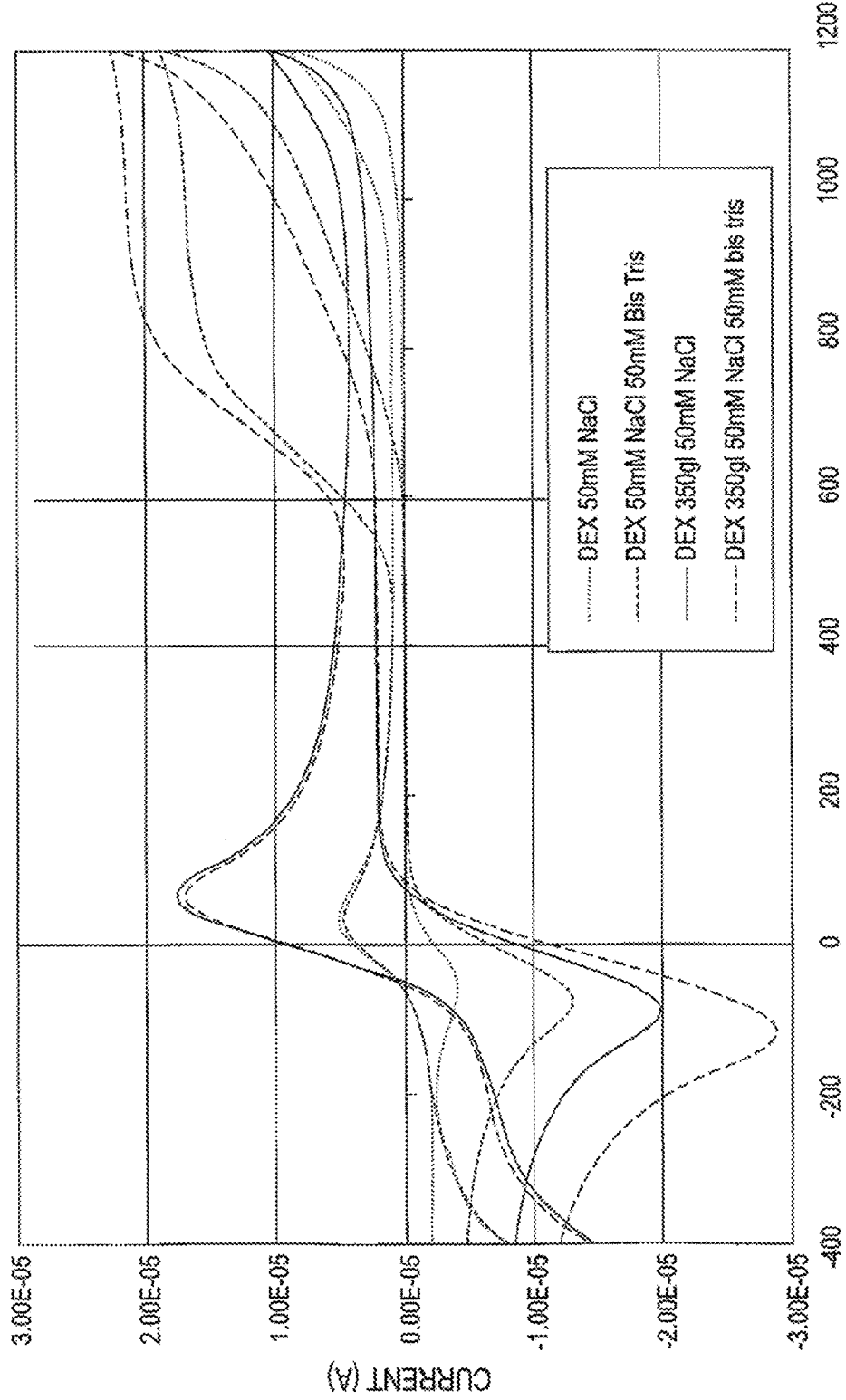
FIG. 7 is a cyclic voltammogram described in Example 3.

Examples 1 and 2 shown in FIGS. 5 and 6 show the presence of the internal reference (Bis-Tris) in solutions with or without glucose, but in the absence of the glucose oxidase and mediator needed to detect the presence of glucose. In the example shown in FIG. 7, the solutions of Examples 1 and 2 were used, but glucose oxidase and potassium ferricyanide (mediator) are included, so that when glucose is present, it is oxidized as it is in electrochemical glucose sensors. Comparing FIG. 7 with FIG. 6, the voltammetric characteristics as seen in the cyclic voltammograms (current versus potential patterns) differ significantly. The peaks in oxidation current occurring around zero volts indicate that glucose is being oxidized. When no glucose was present, only a small current was produced as the potential was moved above 0 mV due to some background activity. When 350 mg/dL of glucose is present, a significant amount of current is produced with the characteristic peaks above, and below 0 mV. A steady state condition was reached at about +400 mV, which could be used to correlate with the amount of glucose present. At both 0 and 350 mg/a, glucose levels, the oxidation currents before 400 mV are the same with and without the addition of the internal reference compound. When the potential reaches +600 mV, the current observed with solutions containing Bis-Tris is always higher than those without Bis-Tris, whether the glucose concentration is 0 or 350 mg/dL. Thus, the control solution that contains the internal reference compound can be identified.

Example 4

Figure 8:
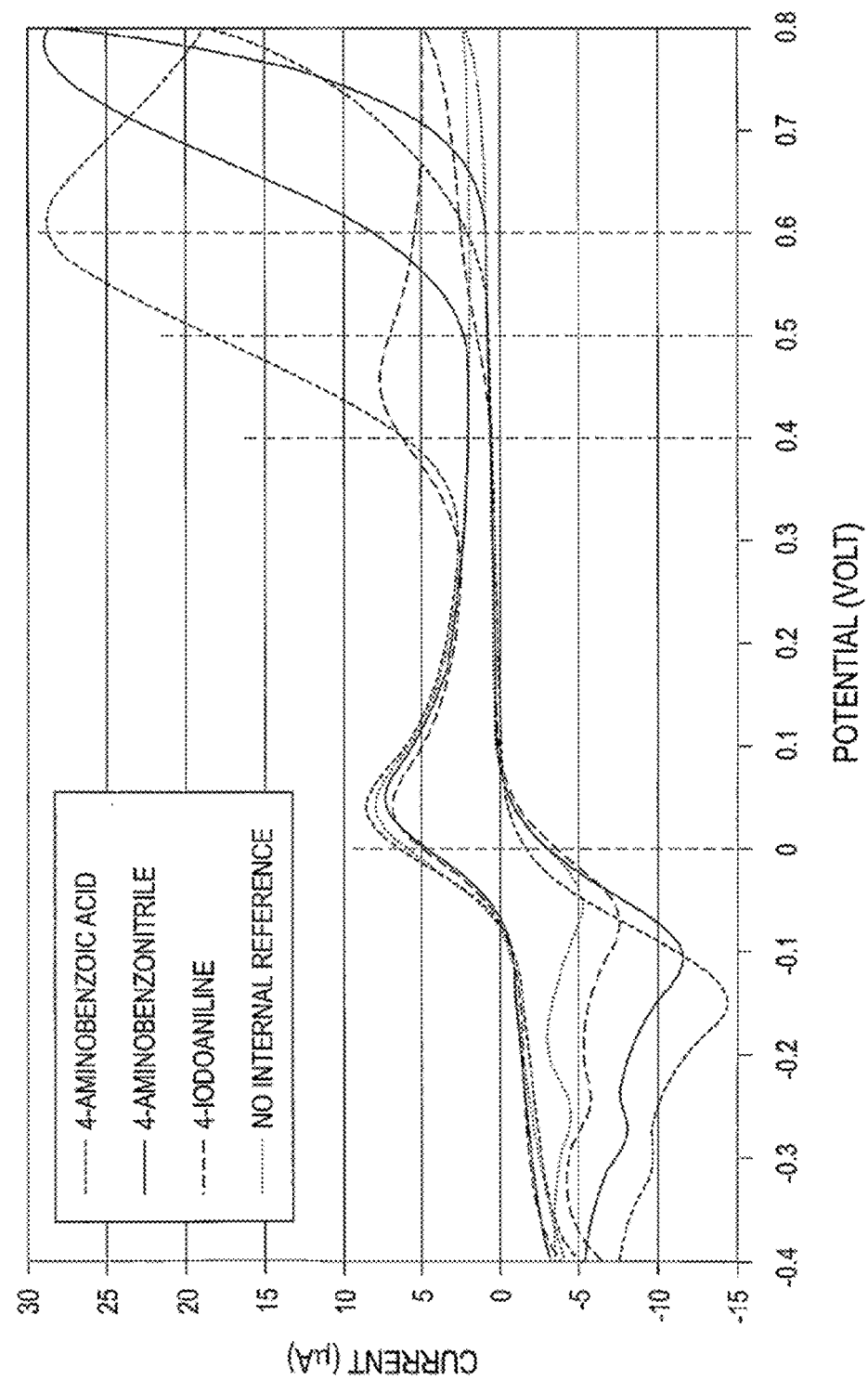
FIG. 8 is a cyclic voltammogram described in Example 4.

Bis-Tris was used as a reference compound in Examples 1-3. In this example, several other internal reference compounds are shown. FIG. 8 shows cyclic voltammograms of three additional internal reference compounds. 4-aminobenzoic acid, 4-aminobenzonitrile and 4-iodoaniline. These three cyclic voltammograms were obtained from the commercial glucose sensor strips of Ascensia AUTODISC® (DEX). The three internal reference species were added individually to a control-equivalent solution of 20-24% PVP polymer, pH 5-5.5 in citrate buffer, but without glucose. The concentrations of 4-aminobenzoic acid, 4-aminobenzenitrile, and 4-iodoaniline each were 50 mM. It can be seen from FIG. 8 that while the first oxidation peaks right after zero volt are substantially identical, the currents after +0.3 volts differ depending on the internal reference compound included. In FIG. 8, the potential between 0.1V and 0.3V is considered as low potential which is used to measure glucose by oxidizing the mediator only. The potential starting at +0.4 volt to +0.8 volt is considered the high potential responsible for oxidizing both the mediator and the internal reference. In the potential region of +0.3 to +0.8 volt, all of the currents are higher when an internal reference was present than when no internal reference added to the control solution.

Example 5

Figure 9A:
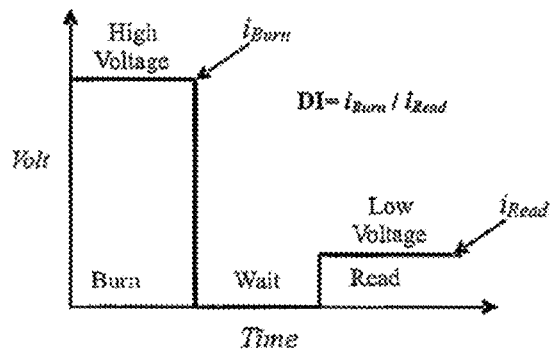
FIG. 9A-E, illustrate potential sequences described in Example 5.
Figure 9B:
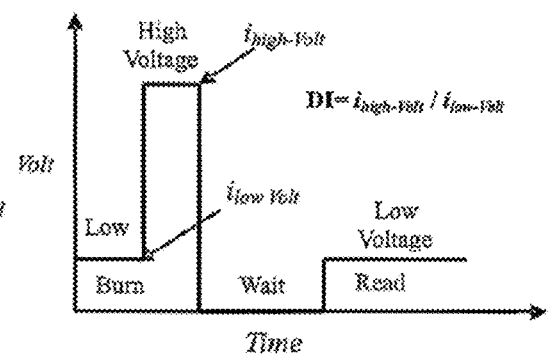
Figure 9C:
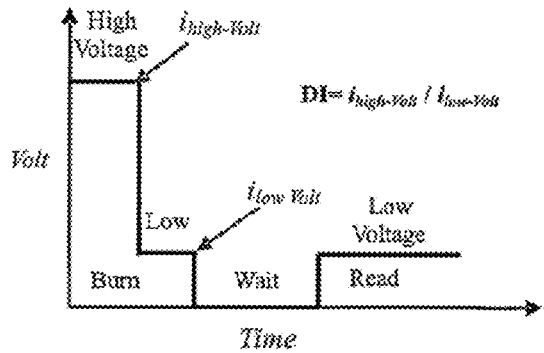
Figure 9D:
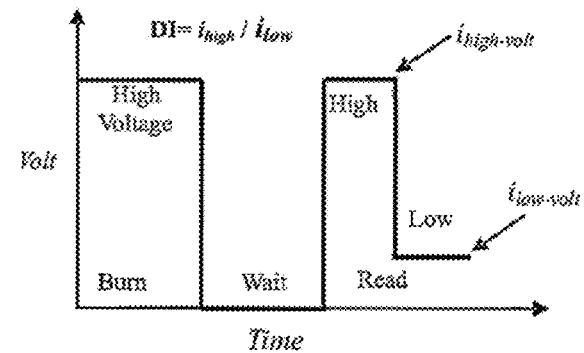
Figure 9E:
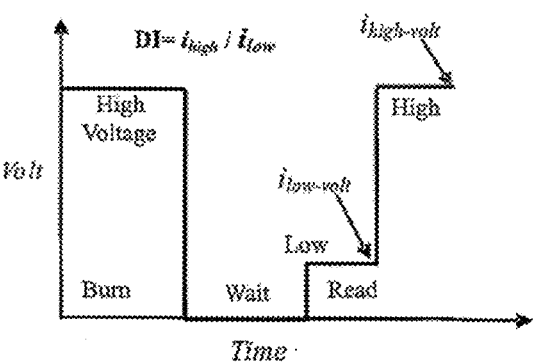

There are many ways of combining high and low potentials to oxidize and measure the internal reference in order to detect the presence of a control solution while still measuring the glucose concentration. FIG. 9A-E show some of the potential sequences (wave forms) for combining high and low potentials. In each case a "burn" period is followed by a waiting period and then a "read" period as has been described earlier. FIG. 9A shows a potential sequence with the high voltage in the Burn period and low voltage in the Read period, which is equivalent to the simple Burn-Wait-Read potential sequence. FIG. 9B shows a potential sequence with the low voltage in the first half of Burn period followed by a high voltage in the same Burn period. In FIG. 9C, a potential sequence with the high voltage in the first half of Burn period is followed by a low voltage in the same Burn period. FIG. 91D shows a potential sequence with the high voltage in the first half of Read period followed by a low voltage in the same Read period. In FIG. 9E, a similar potential sequence is shown with the low voltage in the first half of Read period followed by a high voltage in the same Read period.

Example 6

Figure 10A:
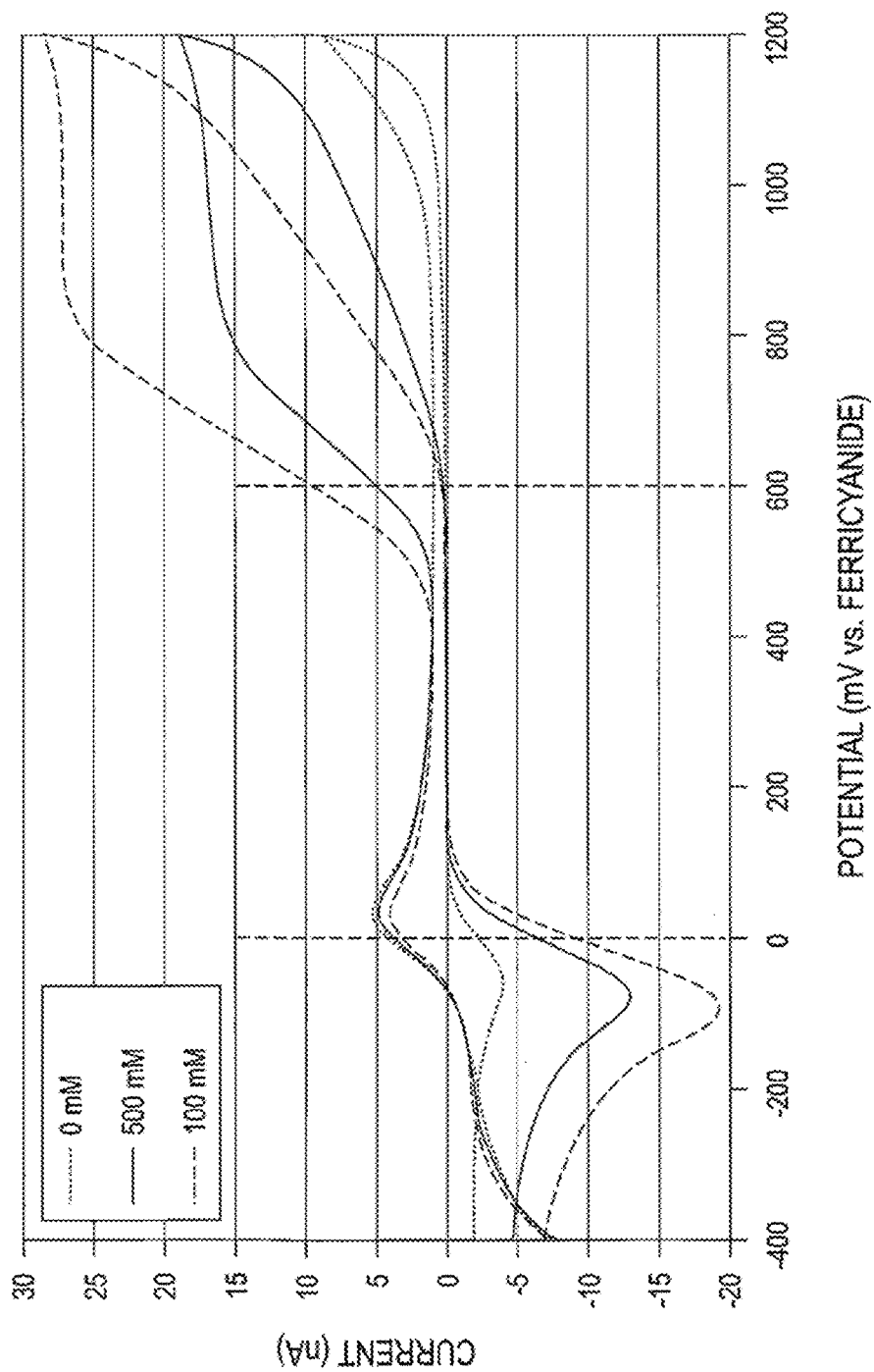
FIG. 10a-b are cyclic voltammograms described in Example G.
Figure 10B:
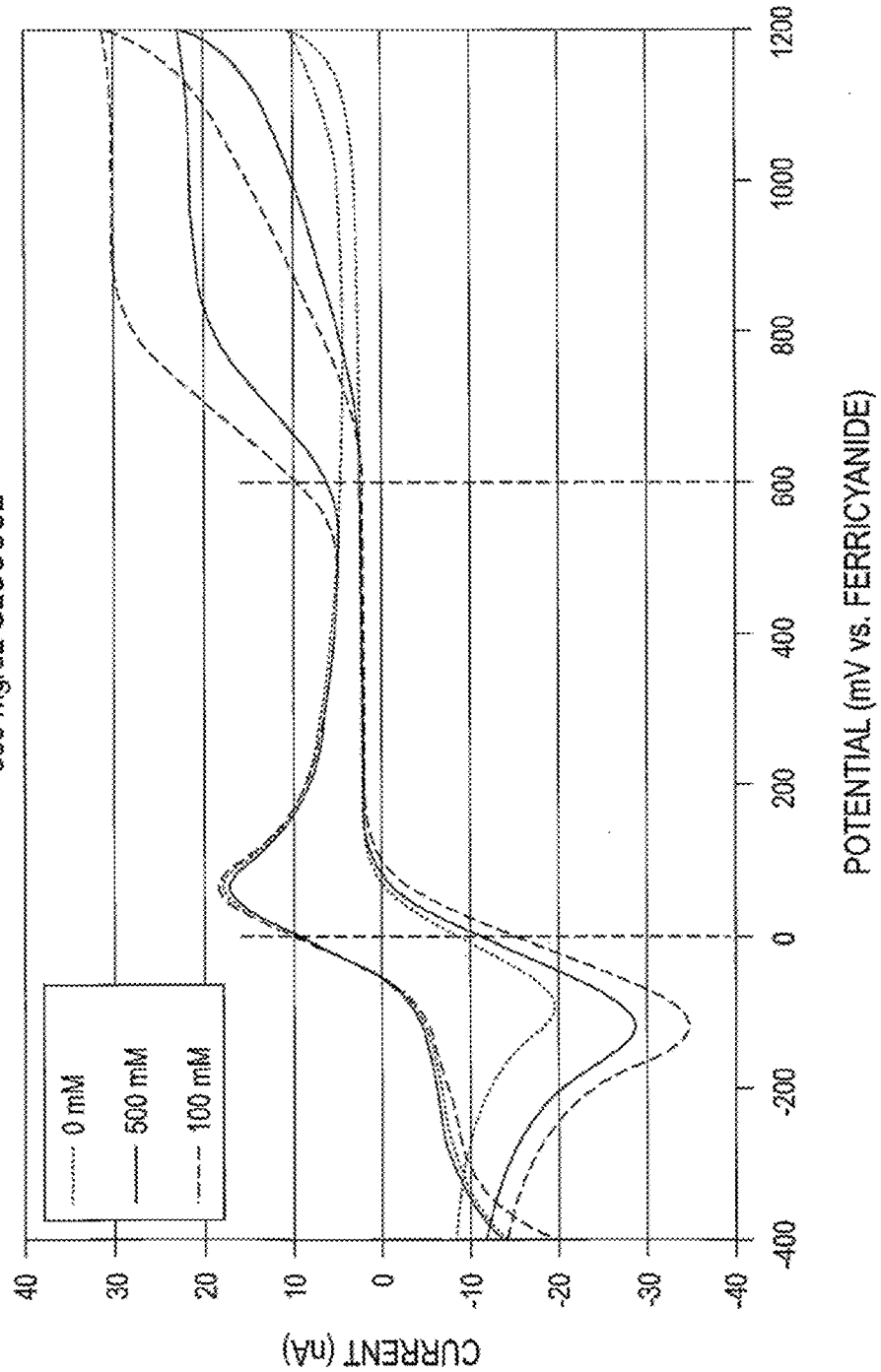

FIGS. 10a-b illustrate the effect of increasing the concentration of the internal reference, in this case Bis-Tris. In FIG. 10a, a control-equivalent solution (that is, without glucose) containing 50 mM NaCl shows the effect of increasing concentration of internal reference from 0 to 50 mM and to 1.00 mM of Bis-Tris (with 100 mM NaCl). The presence of Bis-Tris is dearly visible and increasing its concentration further increases the current at +600 mV. In FIG. 10b, 350 mg/dL of glucose is present in the control solution of the same composition, as indicated by the strong peaks just above 0 mV. Since the glucose current is still notable at about +600 mV, detecting the presence of Bis-Tris requires a larger amount than when no glucose is present. Thus, the concentration of the internal reference should be such that a clear indication of its presence can be detected when the control solution contains a high glucose concentration. Then, when the control solution contains a lower glucose concentration, the presence of the internal reference will be even more evident.

Example 7

Figure 11:
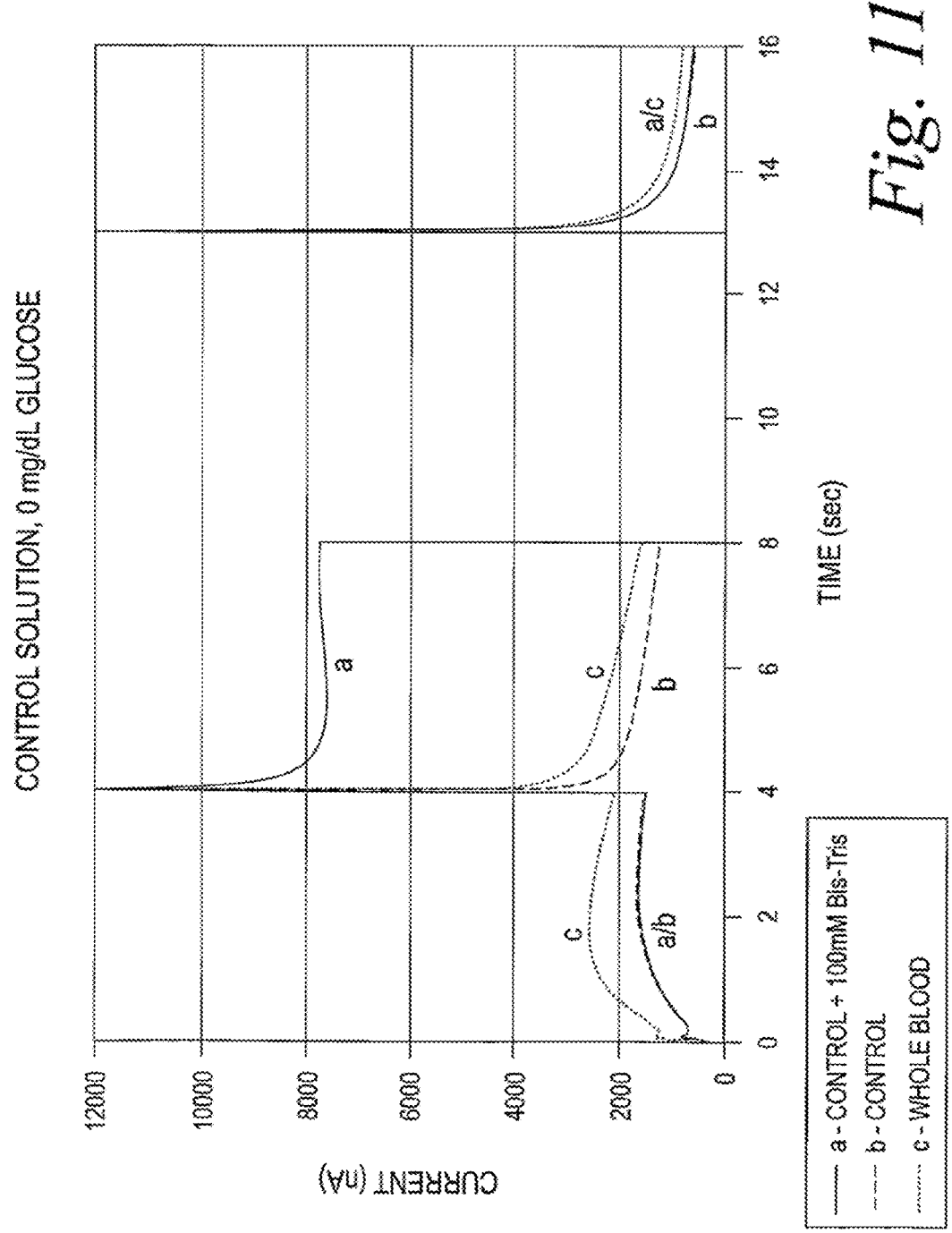
FIG. 11 is a plot of the current versus time obtained in Example 7.

For this example, tests were run comparing control solutions with and without added Bis-Tris as the internal reference and a whole blood sample. In all three cases, the samples were Ascensia AUTODISC® commercial test strips. The test sequence was to apply a potential of +400 mV for 4 seconds, then +600 my for 4 seconds, rest at open circuit (no applied potential to the electrode) for 5 seconds, and then apply +200 mV for 5 seconds. Current profiles for the three types of samples are shown in FIG. 11. The Differential Index (DI) was calculated for two comparisons. Case I-a: the current measured at 8 seconds of the burn period is compared to the current at 4 seconds of the burn period. Case the current measured at 8 seconds of the burn period is compared to the current at 2 seconds of the read period. No glucose was added to the test solution of 100 mM. NaCl and 100 mM Bis-Tris or to the whole blood sample. Case is equivalent to the sequence of FIG. 9B, while Case I-b is equivalent to FIG. 9A. The DI values and the relative changes of the DI values of these tests are shown in Table 2. In both cases, the DI value of the control solution with the internal reference Bis-Tris is in the order of 500% of the DI values found when the control solution and whole blood sample contained no internal reference. These results indicate the control solution with the internal reference can be readily detected, compared with a control solution or whole blood lacking the reference compound.

TABLE 2

DI Values and %-Change of DI value at 0 glucose

| | Test Solution | | |
|---|---|---|---|
| | With Bis-Tris | No. Bis-Tris | Whole Blood |
| B8/B4, DI (Case I-a) | 5.5 | 0.8 | 0.8 |
| Std. Dev. | 0.6 | 0.1 | 0.08 |
| % C.V. | 11.4 | 10.1 | 10.0 |
| % Change vs internal reference | — | 563 | 603 |
| B8/R2, DI (Case I-b) | 10.7 | 1.7 | 1.8 |
| Std. Dev. | 1.5 | 0.23 | 0.13 |
| % C.V. | 14.1 | 13.6 | 7.5 |
| % Change vs internal reference | — | 522 | 503 |

Example 8

Figure 12:
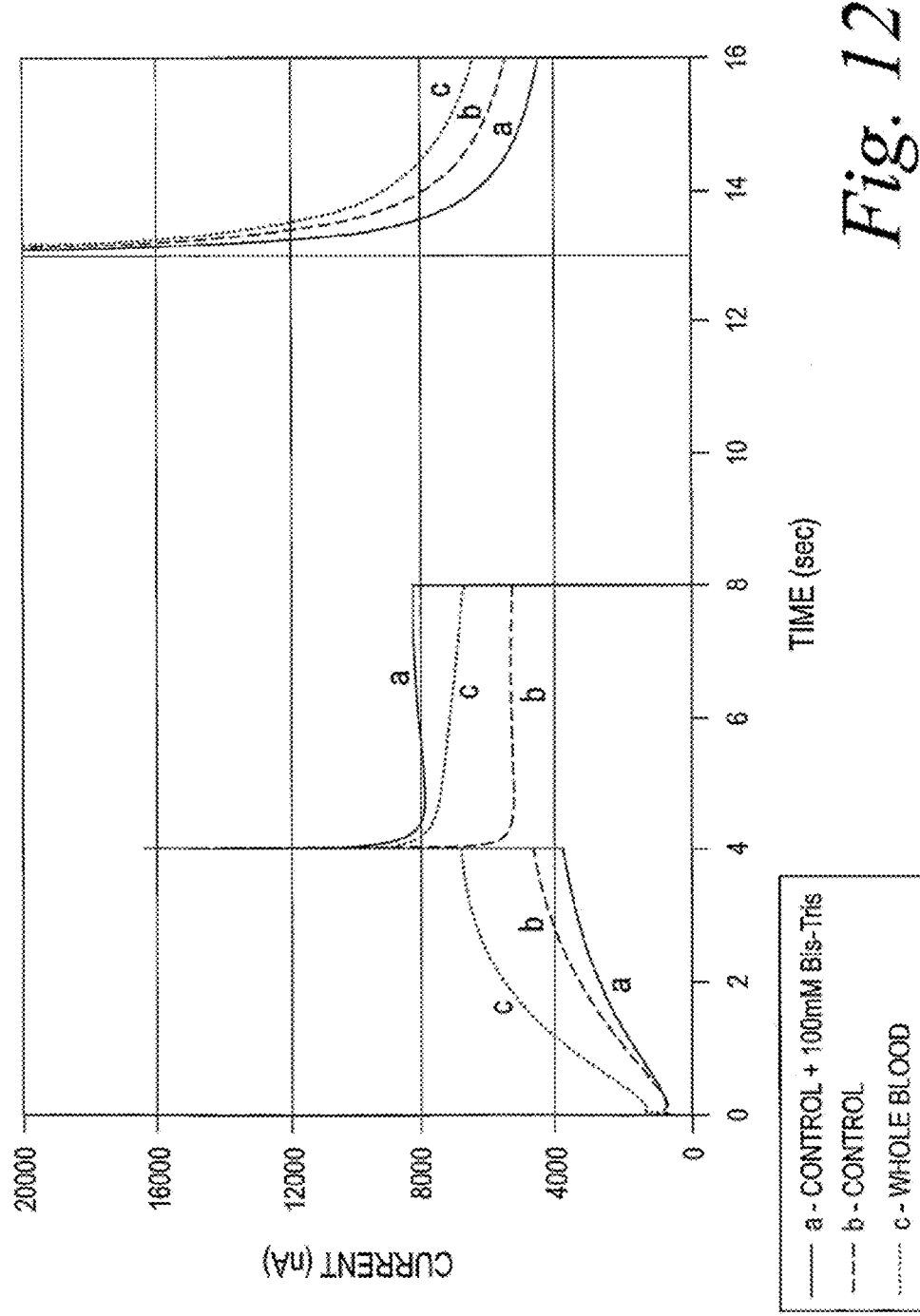
FIG. 12 is a plot of the current versus time obtained in Example 8.

The tests of Example 7 were repeated, but the control solution contained 350 glucose and the whole blood sample 400 mg/dL glucose. The same potential sequence was used for this test. The typical current profiles for the three samples are shown in FIG. 12 for high glucose concentrations. The DI values and the relative change of the DI values are reported in Table 3. The DI values in Table 2 for cases II-a and II-b are the same as in Example 7 and so are the relative changes of DI values with the internal reference to that without the internal reference and the whole blood samples. For the high glucose concentration at 350 mg/dL, the DI value for the control solution with the internal reference is in the order of 100% higher than that of the whole blood samples. This DI difference ensures that the control solution with a internal reference can be distinguished from a control solution lacking the internal reference and the WB sample.

TABLE 3

DI Values and %-Changes of DI Value at High Glucose

| | Control Solution | | |
|---|---|---|---|
| | With Bis-Tris | No. Bis-Tris | Whole Blood |
| B8/B4, DI (Case II-a) | 2.3 | 1.2 | 1.0 |
| Std. Dev. | 0.26 | 0.13 | 0.07 |
| % C.V. | 11.6 | 11.0 | 7.0 |
| % Change vs internal reference | — | 96 | 127 |
| B8/R2, DI (Case II-b) | 1.7 | 0.9 | 0.9 |
| Std. Dev. | 0.09 | 0.03 | 0.03 |
| % C.V. | 5.5 | 3.9 | 3.1 |
| % Change vs internal reference | — | 95 | 78 |

Protocols for Control Solution Testing

Comparing the currents produced during the burn and read periods could be done in many ways. Some test sequences are illustrated in Example 5 and FIG. 9. In the simplest alternative, one measurement is made at the potential needed to oxidize the internal reference compound and another measurement is made at the lower potential used to oxidize the analyte. Then the Differential Index is calculated and, based on the results, the electrochemical meter reports either that a control solution or that a biological sample is being tested. Preferably, the first measurement is made during the later portion of the burn period and the second during the read period, but both measurements could be taken during the burn period or during the read period. The length of time required to obtain current readings may be varied, for example between about 1 and 10 seconds. However, as long as the current readings are long enough to properly represent the presence of the internal reference compound or the glucose, any time period may be used.

For additional reliability in the results, more than one period may be used for both the high and low potentials. That is, the potential for oxidizing the internal reference, say +600 mV for Bis-Tris, and the potential for oxidizing glucose, say +200-400 mV may be applied more than once during the burn period or the read period.

It is also feasible to apply potentials that are higher than are required for the oxidation of the analyte or the internal reference. That is, if the oxidation potential for the glucose mediator is +20 mV, for example, then a potential of +200 mV and higher could be used with the limit being, at the potential at which the internal reference is oxidized.

In one embodiment, multiple variations in the applied potentials are used to provide more consistent indication of the difference between the current measured at high and low potentials. Furthermore, cycling the potentials has the advantage of smoothing the current versus time curves and improving accuracy. For example, the applied potential may be cycled between the high and low values every 0.1 second during the burn and/or read periods.

Alternative Process A

A method of distinguishing a control solution from a biological sample during operation of an electrochemical sensor measuring the amount of an analyte in said control solution and in said biological sample, the method comprising the acts of:

(a) adding to said control solution an internal reference compound, said compound being adapted to be electrochemically oxidized at a potential higher than the potential needed to measure the oxidation of said analyte, said internal reference compound being added in an amount relative to a predetermined amount of analyte in said control solution sufficient to indicate the presence of said internal reference compound in the control solution;

(b) introducing said control solution containing said internal reference compound and said predetermined amount of said analyte to an electrochemical sensor, said sensor having working and reference electrodes and a reaction layer containing reagents for oxidizing said analyte;

(c) at least once applying a potential to said electrodes of said electrochemical sensor sufficient to oxidize said internal reference compound and said analyte and measuring the resulting electrical current;

(d) at least once applying a potential to said electrochemical sensor lower than the potential of (c), said potential being sufficient to measure oxidation of said analyte and not sufficient to oxidize said internal reference compound and measuring the resulting electrical current;

(e) calculating a Differential index (DI) defined as $DI = i_{high\ volt}/i_{low\ volt}$ where: $i_{high\ volt}$ is the current measured in (c)

$i_{low\ volt}$ is the current measured in (d)

(f) determining that a control solution is present when the Differential Index of (e) is sufficiently greater than 1 to distinguish the internal reference compound from the predetermined amount of analyte; and (g) determining that a biological sample is present when the Differential index of (e) is about 1.

Alternative Process B

The method of Alternative Process A, wherein said Differential. Index determined in (f) is 1.5 or higher.

Alternative Process C

The method of Alternative Process A, wherein said internal reference compound is added in an amount proportional to the amount of the analyte present in said control solution.

Alternative Process D

The method of Alternative Process C, wherein said internal reference compound is added in an amount such that the Differential Index is 1.5 or higher when the amount of the analyte is the maximum used in said control solution.

Alternative Process E

The method of Alternative Process A, wherein the potential of (c) is applied before the potential of (d) is applied.

Alternative Process F

The method of Alternative Process A, wherein the potential of (d) is applied before the potential of (c).

Alternative Process G

The method of Alternative Process A, wherein the potentials of (c) and (d) are applied more than once.

Alternative Process H

The method of Alternative Process A, wherein said analyte is measured by applying a first potential sufficient to oxidize said analyte for a first predetermined period of time, followed by applying a second potential insufficient to oxidize said analyte and lower than said first potential for a second predetermined period of time and followed by applying a third potential higher than said second potential and sufficient to oxidize said analyte for a third predetermined period of time.

Alternative Process I

The method of Alternative Process H, wherein said potential of (c) is applied during said first predetermined period of time and said potential of (d) is applied during said third predetermined period of time.

Alternative Process J

The method of Alternative Process H, wherein both said potential of (c) and said potential of (d) are applied during said first predetermined period of time.

Alternative Process K

The method of Alternative Process H, wherein both said potential of (c and said potential of (d) are applied during said third period of time.

Alternative Process L

The method of Alternative Process wherein said potential of (d) is applied during said first determined period of time and said potential of (c) is applied during said third period of time.

Alternative Process M

The method of Alternative Process H, wherein said potentials of at least one of (c) and (d) is applied more than one time.

Alternative Process N

The method of Alternative Process A, wherein said analyte is glucose and said biological sample is whole blood.

Alternative Process O

The method of Alternative Process A, wherein said internal reference compound is an oxidizable organo-metallic compound, coordination compound, or organic amine compound.

Alternative Process P

The method of Alternative Process O, wherein said internal reference compound is said organic amine compound, said organic amine compound being 3-(N-morpholino) propane sulfonic acid, N-(2-hydroxyethyl) piperazine-$N^1$-(2-ethane sulfonic acid), 2-[(2-Hydroxy-1,1-bis(hydroxy methyl)ethylamino]ethane sulfonic acid, 2-Morpholino ethane sulfonic acid, and Bis(2-hydroxyethyl)amino-tris(hydroxymethyl) methane [Bis-Tris], 4-aminobenzonitrile, 4-aminobenzoic acid, or 4-iodoaniline.

Alternative Process Q

The method of Alternative Process P, wherein said internal reference compound is Bis Tris.

Alternative Process R

The method of Alternative Process O, wherein said internal reference compound is said oxidizable organo-metallic compound, said oxidizable organometallic compound being ferrocene or ferrocene derivatives.

Alternative Process S

The method of Alternative Process O, wherein said internal reference compound is said coordination compound, said coordination compound being potassium ferrocyanide.

Alternative Process T

The method of Alternative Process N, wherein glucose is oxidized by glucose oxidase and wherein said control solution contains a buffer capable of maintaining a pH between 5 and 7.

Alternative Process U

The method of Alternative Process N, wherein glucose is oxidized by glucose dehydrogenase and wherein said control solution contains a buffer capable of maintaining a pH between 6 and 8.

Alternative Embodiment V

A control solution for use in testing an electrochemical system for measuring the amount of an analyte in a biological sample, the control solution comprising:
 (a) a predetermined amount of said analyte; and
 (b) a predetermined, amount of an internal reference compound, said internal reference compound being adapted to be oxidized at a potential higher than the potential required to oxidize said analyte, said predetermined amount of said internal reference compound being proportional to said predetermined amount of analyte such that the presence of said internal reference compound is detectable.

Alternative Embodiment W

The control solution of Alternative Embodiment V, wherein said analyte is glucose and said biological sample is whole blood.

Alternative Embodiment X

The control solution of Alternative Embodiment W, wherein said internal reference compound is an oxidizable organo-metallic compound, coordination compound, or organic amine compound.

Alternative Embodiment Y

The control solution of Alternative Embodiment X, wherein said internal reference compound is said organic amine compound, said organic amine compound being 3-(N-morpholino) propane sulfonic acid, N-(2-hydroxyethyl) piperazine-$N^1$-(2-ethane sulfonic acid), 2-[(2-Hydroxy-1,1-bis(hydroxy methyl)ethylamino]ethane sulfonic acid, 2-Morpholino ethane sulfonic acid, and Bis(2-hydroxyethyl)amino-tris(hydroxymethyl)methane [Bis-Tris], 4-aminobenzonitrile, 4-aminobenzoic acid, or 4-iodoaniline.

Alternative Embodiment Z

The control solution of Alternative Embodiment Y, wherein said internal reference is Bis-Tris.

Alternative Embodiment AA

The control solution of Alternative Embodiment X, wherein said internal reference compound is said oxidizable organo-metallic compound, said oxidizable organo-metallic compound being ferrocene or ferrocene derivatives.

Alternative Embodiment BB

The control solution of Alternative Embodiment X, wherein said internal reference compound is said coordination compound, said coordination compound being potassium ferrocyanide.

Alternative Embodiment CC

The control solution of Alternative Embodiment W, wherein glucose is oxidized by glucose oxidase and a buffer is included to maintain pH between 5 and 7.

Alternative Embodiment DD

The control solution of Alternative Embodiment W, wherein glucose is oxidized by glucose dehydrogenase and a buffer is included to maintain pH between 6 and 8.

Alternative Embodiment EE

An internal reference compound for addition to a control solution used to test a electrochemical glucose meter, said internal reference comprising a chemical compound that is oxidizable at a potential higher than that required to measure the oxidation of glucose.

Alternative Embodiment FF

The internal reference of Alternative Embodiment EE, wherein said internal reference is oxidizable at a potential at least 100 mV greater than the potential required to measure the oxidation of glucose.

Alternative Embodiment GG

The internal reference Alternative Embodiment EE, wherein said internal reference compound is an oxidizable organo-metallic compound, coordination compound, or organic amine compound.

Alternative Embodiment HH

The internal reference of Alternative Embodiment GG, wherein said internal reference compound is 3-(N-morpholino) propane sulfonic acid, N-(2-hydroxyethyl) piperazine-$N^1$-(2-ethane sulfonic acid), 2-[(2-Hydroxy-1,1-bis(hydroxy methyl)ethylamino]ethane sulfonic acid, 2-Morpholino ethane sulfonic acid, and Bis(2-hydroxyethyl)amino-tris(hydroxymethyl) methane [Bis-Tris], 4-aminobenzonitrile, 4-aminobenzoic acid, and 4-iodoaniline.

Alternative Embodiment II

The internal reference of Alternative Embodiment NFL wherein said internal reference compound is Bis-Tris.

Alternative Embodiment JJ

The internal reference of Alternative Embodiment GG, wherein said internal reference compound is said oxidizable organo-metallic compound, said oxidizable organometallic compound being ferrocene or ferrocene derivatives.

Alternative Embodiment KK

The internal reference of Alternative Embodiment GG, wherein said internal reference compound is said coordination compound, said coordination compound being potassium ferrocyanide.

While the invention is susceptible to various modifications and alternative forms, specific embodiments are shown by way of example in the drawings and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A control solution for use with an electrochemical system, the electrochemical system configured to measure the amount of an analyte in a sample, the control solution comprising:
   (a) a predetermined amount of the analyte; and
   (b) a predetermined amount of an internal reference compound, the predetermined amount of the internal reference compound being dependent upon the predetermined amount of analyte such that the presence of said internal reference compound is detectable by the electrochemical system, the internal reference compound having a redox potential that is at least 100 mV higher than the potential required to measure oxidation of the analyte, such that the control solution is distinguishable from the sample based on one or more currents generated in response to one or more potentials applied to the control solution by the electrochemical system.

2. The control solution of claim 1, wherein the electrochemical system includes a reagent system having a ruthenium hexamine mediator and the internal reference compound includes potassium ferrocyanide, ferrocene, its derivatives, or combinations thereof.

3. The control solution of claim 1, wherein the electrochemical system includes a reagent system having a ferricyanide mediator and the internal reference compound includes Bis-Tris, 4-amino benzonitrile, or combinations thereof.

4. The control solution of claim 1, wherein the analyte is glucose and the sample is whole blood.

5. The control solution of claim 1, wherein the internal reference compound is an oxidizable organo-metallic compound, coordination compound, or organic amine compound.

6. The control solution of claim 5, wherein the internal reference compound is the organic amine compound, the organic amine compound being 3-(N-morpholino) propane sulfonic acid, N-(2-hydroxyethyl) piperazine-$N^1$-(2-ethane sulfonic acid), 2-[(2-Hydroxy-1,1-bis(hydroxy methyl)ethylamino]ethane sulfonic acid, 2-Morpholino ethane sulfonic acid, and Bis(2-hydroxyethyl)amino-tris(hydroxymethyl) methane [Bis-Tris], 4-aminobenzonitrile, 4-aminobenzoic acid, or 4-iodoaniline.

7. The control solution of claim 6, wherein the internal reference compound is Bis-Tris.

8. The control solution of claim 5, wherein the internal reference compound is the oxidizable organo-metallic compound, the oxidizable organo-metallic compound being ferrocene or ferrocene derivatives.

9. The control solution of claim 5, wherein the internal reference compound is the coordination compound, the coordination compound being potassium ferrocyanide.

10. The control solution of claim 4, the control solution further comprising a buffer to maintain pH between 5 and 7 and the reagent system includes glucose oxidase.

11. The control solution of claim 4, the control solution further comprising a buffer to maintain pH between 6 and 8 and the reagent system includes glucose dehydrogenase.

12. The control solution of claim 1, further comprising a buffer, the internal reference compound being different from the buffer, the internal reference compound and the buffer being configured to serve different functions.

13. A control solution for use with an electrochemical system, the electrochemical system configured to measure the amount of glucose in a whole blood sample, the control solution comprising:
    a predetermined amount of glucose;
    a predetermined amount of an internal reference compound, the predetermined amount of the internal reference compound being dependent upon the predetermined amount of glucose such that the presence of said internal reference compound is detectable by the electrochemical system, the internal reference compound having a redox potential that is at least 100 mV higher than the potential required to measure oxidation of the glucose, the internal reference compound being configured to distinguish the control solution from the sample based on one or more currents generated in response to one or more potentials applied to the control solution by the electrochemical system; and a buffer configured to assist in oxidizing the glucose.

14. The control solution of claim 13, wherein the electrochemical system includes a reagent system having a ruthenium hexamine mediator, and the internal reference compound includes potassium ferrocyanide, ferrocene, its derivatives, or combinations thereof.

15. The control solution of claim 13, wherein the electrochemical system includes a reagent system having a ferricyanide mediator, and the internal reference compound includes Bis-Tris, 4-amino benzonitrile, or combinations thereof.

16. The control solution of claim 13, wherein the internal reference compound is an oxidizable organo-metallic compound, coordination compound, or organic amine compound.

17. The control solution of claim 16, wherein the internal reference compound is the organic amine compound, the organic amine compound being 3-(N-morpholino) propane sulfonic acid, N-(2-hydroxyethyl) piperazine-$N^1$-(2-ethane sulfonic acid), 2-[(2-Hydroxy-1,1-bis(hydroxy methyl)ethylamino]ethane sulfonic acid, 2-Morpholino ethane sulfonic acid, and Bis(2-hydroxyethyl)amino-tris(hydroxymethyl) methane [Bis-Tris], 4-aminobenzonitrile, 4-aminobenzoic acid, or 4-iodoaniline.

18. The control solution of claim 17, wherein the internal reference compound is Bis-Tris.

19. The control solution of claim 16, wherein the internal reference compound is the oxidizable organo-metallic compound, the oxidizable organo-metallic compound being ferrocene or ferrocene derivatives.

20. The control solution of claim 16, wherein the internal reference compound is the coordination compound, the coordination compound being potassium ferrocyanide.

21. The control solution of claim 13, the internal reference compound being different from the buffer, the internal reference compound and the buffer being configured to serve different functions.

* * * * *